(12) United States Patent
Lee et al.

(10) Patent No.: US 6,833,257 B2
(45) Date of Patent: Dec. 21, 2004

(54) FLUORIMETRIC DETECTION SYSTEM OF A NUCLEIC ACID

(75) Inventors: Martin A Lee, Salisbury (GB); Roderick Fuerst, Kimbolton (GB)

(73) Assignee: The Secretary of State for Defence, Hampshire (GB)

( * ) Notice: Subject to any disclaimer, the term of this patent is extended or adjusted under 35 U.S.C. 154(b) by 0 days.

(21) Appl. No.: 09/555,123

(22) PCT Filed: Nov. 27, 1998

(86) PCT No.: PCT/GB98/03560

§ 371 (c)(1),
(2), (4) Date: May 25, 2000

(87) PCT Pub. No.: WO99/28500

PCT Pub. Date: Jun. 10, 1999

(65) Prior Publication Data

US 2002/0119450 A1 Aug. 29, 2002

(30) Foreign Application Priority Data

Nov. 29, 1997 (GB) .............................. 9725197

(51) Int. Cl.[7] .............................................. C12D 19/34
(52) U.S. Cl. ...................... 435/91.1; 435/6; 435/91.2; 435/183; 435/270; 436/501; 436/94; 436/800; 536/23.1; 536/24.3; 536/24.31; 536/24.33; 536/25.3
(58) Field of Search ......................... 435/6, 91.1, 91.2, 435/183, 270; 436/501, 94, 800; 536/23.1, 24.3, 24.31, 24.33, 25.3

(56) References Cited

U.S. PATENT DOCUMENTS

| | | | |
|---|---|---|---|
| 4,868,103 A | | 9/1989 | Stavrianopoulos et al. |
| 5,491,063 A | | 2/1996 | Fisher et al. |
| 5,567,583 A | * | 10/1996 | Wang et al. .................. 435/6 |
| 6,403,311 B1 | * | 6/2002 | Chan ............................ 435/6 |

FOREIGN PATENT DOCUMENTS

| | | |
|---|---|---|
| EP | 0 512 334 | 11/1992 |
| EP | 0 512 334 A | 11/1992 |
| EP | 0 745 690 A2 | 12/1996 |
| WO | 95 08642 | 3/1995 |
| WO | WO 95 08642 A | 3/1995 |
| WO | 97 12030 | 4/1997 |
| WO | WO 97 12030 A | 4/1997 |

OTHER PUBLICATIONS

Vaughan et al, "Human Antibodies with Sub–nanomolar Affinities . . . ", Nature Biotechnology, vol. 14, Mar., 1996.
Cardullo et al, "Detection of nucleic acid hybridization . . . ", Proc. Natl. Acad. Sci. USA, vol. 85, pp. 8790–8794, Dec., 1988.
Gelmini et al, "Quantitative polymerase chain reaction–based homogeneous . . . ", Clinical Chemistry, 43:5 752–758 (1997).
Bassam et al, "Nucleic Acid Sequence Detection Systems: Revolutionary . . . ", Australasian Biotechnology, vol. 6, No. 5, Oct., 1996.

* cited by examiner

*Primary Examiner*—Bradley L. Sisson
(74) *Attorney, Agent, or Firm*—Nixon & Vanderhye P.C.

(57) ABSTRACT

A method for detecting the presence of a target nucleic acid sequence in a sample, said method comprising:
  (a) adding to a sample suspected of containing said target nucleic acid sequence, a probe specific for said target sequence and DNA duplex binding agent, said probe comprising a reactive molecule able to absorb fluorescence from or donate fluorescent energy to said DNA duplex binding agent,
  (b) subjecting the thus formed mixture to an amplification reaction in which target nucleic acid is amplified,
  (c) subjecting said sample to conditions under which the said probe hybridizes to the target sequence, and
  (d) monitoring fluorescence from said sample.
This method can be used for example to monitor amplification reactions such as PCR reactions, such that the amount of target sequence present in the sample may be determined. Additionally or alternatively, it may be used to generate duplex destabilization data such as melt hysteresis information for amplification monitoring or for detection and quantitation of polymorphisms or allelic variation, and so is useful in genetic diagnosis.

16 Claims, 3 Drawing Sheets

FLUORIMETRIC DETECTION SYSTEM OF A NUCLEIC ACID

The present application is a 371 U.S. national phase of International Application No. PCT/GB98/03560, filed Nov. 27, 1998.

The present invention provides a method for detecting a target polynucleotide in a sample, for example by quantitatively monitoring an amplification reaction, as well as to probes and kits for use in these methods. The method is particularly suitable for the detection of polymorphisms or allelic variation and so may be used in diagnostic methods Known fluorescence polymerase chain reaction (PCR) monitoring techniques include both strand specific and generic DNA intercalator techniques that can be used on a few second-generation PCR thermal cycling devices.

Generic methods utilise DNA intercalating dyes that exhibit increased fluorescence when bound to double stranded DNA species. Fluorescence increase due to a rise in the bulk concentration of DNA during amplifications can be used to measure reaction progress and to determine the target molecule copy number. Furthermore, by monitoring fluorescence with a controlled change of temperature, DNA melting curves can be generated, for example, at the end of PCR thermal cycling.

When generic DNA methods are used to monitor the rise in bulk concentration of nucleic acids, these processes can be monitored with a minimal time penalty (compared to some other known assays discussed below). A single fluorescent reading can be taken at the same point in every reaction. End point melting curve analysis can be used to discriminate artifacts from amplicon, and to discriminate amplicons. Melting peaks of products can be determined for concentrations that cannot be visualized by agarose gel electrophoresis.

In order to obtain high resolution melting data, for example for multiple samples, the melt experiment must be performed slowly on existing hardware taking up to five minutes. However, by continually monitoring fluorescence amplification, a 3D image of the hysteresis of melting and hybridization can be produced. This 3D image is amplicon dependent and may provide enough information for product discrimination.

It has been found that DNA melting curve analysis in general is a powerful tool in optimizing PCR thermal cycling. By determining the melting temperatures of the amplicons, it is possible to lower the denaturing temperature in later PCR cycles to this temperature. Optimization for amplification from first generation reaction products rather than the target DNA, reduces artifact formation occurring in later cycles. Melting temperatures of primer oligonucleotides and their complements can be used to determine their annealing temperatures, reducing the need for empirical optimization.

The generic intercalator methods however are only quasi-strand-specific and therefore is not very useful where strand specific detection is required.

Strand specific methods utilise additional nucleic acid reaction components to monitor the progress of amplification reactions. These methods often use fluorescence energy transfer (FET) as the basis of detection. One or more nucleic acid probes are labeled with fluorescent molecules, one of which is able to act as an energy donor and the other of which is an energy acceptor molecule. These are sometimes known as a reporter molecule and a quencher molecule respectively. The donor molecule is excited with a specific wavelength of light which falls within its excitation spectrum and subsequently it will emit light within its fluorescence emission wavelength. The acceptor molecule is also excited at this wavelength by accepting energy from the donor molecule by a variety of distance-dependent energy transfer mechanisms. A specific example of fluorescence energy transfer which can occur is Fluorescence Resonance Energy Transfer or "FRET". Generally, the acceptor molecule accepts the emission energy of the donor molecule when they are in close proximity (e.g. on the same, or a neighboring molecule). The basis of fluorescence energy transfer detection is to monitor the changes at donor and acceptor emission wavelengths.

There are two commonly used types of FET or FRET probes, those using hydrolysis of nucleic acid probes to separate donor from acceptor, and those using hybridization to alter the spatial relationship of donor and acceptor molecules.

Hydrolysis probes are commercially available as Taqman™ probes. These consist of DNA oligonucleotides that are labeled with donor and acceptor molecules. The probes are designed to bind to a specific region on one strand of a PCR product. Following annealing of the PCR primer to this strand, Taq enzyme extends the DNA with 5' to 3' polymerase activity. Taq enzyme also exhibits 5' to 3' exonuclease activity. TaqMan™ probes are protected at the 3' end by phosphorylation to prevent them from extension. If the TaqMan™ probe is hybridized to the product strand, an extending Taq molecule may also hydrolyze the probe, liberating the donor from acceptor as the basis of detection. The signal in this instance is cumulative, the concentration of free donor and acceptor molecules increasing with each cycle of the amplification reaction.

The fact that signal generation is dependent upon the occurrence of probe hydrolysis reactions means that there is a time penalty associated with this method. Furthermore, the presence of the probe may interrupt the smooth operation of the PCR process.

In addition, it has been found that hydrolysis can become non-specific, particularly where large numbers of amplification cycles, for instance more than 50 cycles, are required. In these cases, non-specific hydrolysis of the probe will result in an unduly elevated signal.

This means that such techniques are not very compatible with rapid PCR methods which are becoming more prominent with the development of rapid hot air thermal cyclers such as the RapidCycler™ and LightCycler™ from Idaho Technologies Inc. Other rapid PCR devices are described for example in co-pending British Patent Application Nos. 9625442.0 and 9716052.7. The merits of rapid cycling over conventional thermal cycling have been reported elsewhere. Such techniques are particularly useful for example in detection systems for biological warfare where speed of result is important if loss of life or serious injury is to be avoided.

Furthermore, hydrolysis probes do not provide significant information with regard to hysteresis of melting since signal generation is, by and large, dependent upon hydrolysis of the probe rather than the melt temperature of the amplicon.

U.S. Pat. No. 5,491,063 describes a method for in-solution quenching of fluorescently labeled probes which relies on modification of the signal from a labeled single stranded oligonucleotide by a DNA binding agent. The difference in this signal which occurs as a result of a reduced chain length of the probe following probe cleavage (hydrolysis) during a polymerase chain reaction is suggested for providing a means for detecting the presence of a target nucleic acid.

Hybridization probes are available in a number of forms. Molecular beacons are oligonucleotides that have complementary 5' and 3' sequences such that they form hairpin loops. Terminal fluorescent labels are in close proximity for FRET to occur when the hairpin structure is formed. Following hybridization of molecular beacons to a complementary sequence the fluorescent labels are separated, so FRET does not occur, and this forms the basis of detection.

Pairs of labeled oligonucleotides may also be used. These hybridize in close proximity on a PCR product strand bringing donor and acceptor molecules together so that FRET can occur. Enhanced FRET is the basis of detection. Variants of this type include using a labeled amplification primer with a single adjacent probe.

The use of two probes, or a molecular beacon type of probe which includes two labeling molecules increases the cost involved in the process. In addition, this method requires the presence of a reasonably long known sequence so that two probes which are long enough to bind specifically in close proximity to each other are known. This can be a problem in some diagnostic applications, where the length of conserved sequences in an organism which can be used to design an effective probe, such as the HIV virus, may be relatively short.

Furthermore, the use of pairs of probes involves more complex experimental design. For example, a signal provided when by the melt of a probe is a function of the melting off of both probes. The study of small mismatches or where one of the probes is required to bind across a splice region (for example to detect RNA as compared to DNA in a sample where the sequence on either side of an intron can be utilised as the probe site) can yield incorrect results if the other probe melts first.

U.S. Pat. No. 4,868,103 describes in general terms, a FRET system for detecting the presence of an analyte, which utilises an intercalating dye as the donor molecule. The process does not involve an amplification stage.

The applicants have developed a strand specific system for detecting the presence of particular nucleic acid sequences.

The invention provides a method for detecting the presence of a target nucleic acid sequence in a sample, said method comprising:

(a) adding to a sample suspected of containing said target nucleic acid sequence, a DNA duplex binding agent, and a probe specific for said target sequence, said probe comprising a reactive molecule able to absorb fluorescence from or donate fluorescent energy to said DNA duplex binding agent, (b) subjecting the thus formed mixture to an amplification reaction in which target nucleic acid is amplified, (c) subjecting said sample to conditions under which the said probe hybridizes to the target sequence, and (d) monitoring fluorescence from said sample.

As used herein, the expression "DNA duplex binding agent" refers to any entity which adheres or associates itself with DNA in duplex form. These include intercalating dyes as are well known in the art.

As the probe hybridizes to the target sequence in step (c), DNA duplex binding agent such as an intercalating dye is trapped between the strands. In general, this would increase the fluorescence at the wavelength associated with the dye. However, where the reactive molecule is able to absorb fluorescence from the dye (i.e. it is an acceptor molecule), it accepts emission energy from the dye by means of FET, especially FRET, and so it emits fluorescence at its characteristic wavelength. Increase in fluorescence from the acceptor molecule, which is of a different wavelength to that of the dye, will indicate binding of the probe in duplex form. Thus changes in fluorescence which are indicative of the formation or destabilization of duplexes involving the probe are preferably monitored in step (d).

Similarly, where the reactive molecule is able to donate fluorescence to the dye (i.e. it is a donor molecule), the emission from the donor molecule is reduced as a result of FRET and this reduction may be detected. Fluorescence of the dye is increased more than would be expected under these circumstances.

Preferably the reactive molecule is an acceptor molecule as the signals are more readily determinable.

The use of a DNA duplex binding agent such as an intercalating dye and a probe which is singly labeled is advantageous in that these components are much more economical than other assays in which doubly labeled probes are required. By using only one probe, the length of known sequence necessary to form the basis of the probe can be relatively short and therefore the method can be used, even in difficult diagnostic situations.

Furthermore the method of the invention is extremely versatile in its applications. The method can be used to generate both quantitative and qualitative data regarding the target nucleic acid sequence in the sample, as discussed in more detail hereinafter. In particular, not only does the invention provide for quantitative amplification, but also it can be used, additionally or alternatively, to obtain characterizing data such as duplex destabilization temperatures or melting points.

In the method of the invention, the sample may be subjected to conditions under which the probe hybridizes to the samples during or after the amplification reaction has been completed. The process therefore allows the detection to be effected in a homogenous manner, in that the amplification and monitoring can be carried out in a single container with all reagents added initially. No subsequent reagent addition steps are required. Neither is there any need to effect the method in the presence of solid supports (although this is an option).

The probe may comprise a nucleic acid molecule such as DNA or RNA, which will hybridize to the target nucleic acid sequence when the latter is in single stranded form. In this instance, step (c) will involve the use of conditions which render the target nucleic acid single stranded.

Probe may either be free in solution or immobilized on a solid support, for example to the surface of a bead such as a magnetic bead, useful in separating products, or the surface of a detector device, such as the waveguide of a surface plasmon resonance detector. The selection will depend upon the nature of the particular assay being looked at and the particular detection means being employed.

In particular, the amplification reaction used will involve a step of subjecting the sample to conditions under which any of the target nucleic acid sequence present in the sample becomes single stranded. Such amplification reactions include the polymerase chain reaction (PCR) or the ligase chain reaction (LCR) but is preferably a PCR reaction.

It is possible then for the probe to hybridize during the course of the amplification reaction provided appropriate hybridization conditions are encountered.

In a preferred embodiment, the probe may be designed such that these conditions are met during each cycle of the amplification reaction. Thus at some point during each cycle of the amplification reaction, the probe will hybridize to the target sequence, and generate a signal as a result of the FET or FRET between it and the DNA duplex binding agent such as the intercalating dye trapped between the probe and the target sequence. As the amplification proceeds, the probe will be separated or melted from the target sequence and so the signal generated by it will reduce. Hence in each cycle of the amplification, a fluorescence peak from the reactive molecule is generated. The intensity of the peak will increase as the amplification proceeds because more target sequence becomes available for binding to the probe.

By monitoring the fluorescence of the reactive molecule from the sample during each cycle, the progress of the amplification reaction can be monitored in various ways. For example, the data provided by melting peaks can be analyzed, for example by calculating the area under the melting peaks and this data plotted against the number of cycles.

For example, the fluorescence is suitably monitored using a known fluorimeter. The signals from these, for instance in the form of photo-multiplier voltages, are sent to a data processor board and converted into a spectrum associated with each sample tube. Multiple tubes, for example 96 tubes, can be assessed at the same time. Data may be collected in this way at frequent intervals, for example once every 10 ms, throughout the reaction.

The spectra generated in this way can be resolved, for example, using "fits" of pre-selected dyes, to form peaks representative of each signaling moiety (i.e. dye and/or reactive molecule). The areas under the peaks can be determined which represents the intensity value for each signal, and if required, expressed as quotients of each other. The differential of signal intensities and/or ratios will allow changes in FRET to be recorded through the reaction or at different reaction conditions, such as temperatures. The changes, as outlined above, are related to the binding phenomenon between the probe and the target sequence. The integral of the area under the differential peaks will allow intensity values for the FRET effects to be calculated.

This data provides the opportunity to quantitate the amount of target nucleic acid present in the sample.

In addition, the kinetics of probe hybridization will allow the determination, in absolute terms, of the target sequence concentration. Changes in fluorescence from the sample can allow the rate of hybridization of the probe to the sample to be calculated. An increase in the rate of hybridization will relate to the amount of target sequence present in the sample. As the concentration of the target sequence increases as the amplification reaction proceeds, hybridization of the probe will occur more rapidly. Thus this parameter also can be used as a basis for quantification. This mode of data processing useful in that it is not reliant on signal intensity to provide the information.

Preferably, the fluorescence of both the dye and the reactive molecule are monitored and the relationship between the emissions calculated. This provides a strand specific measure to complement the generic DNA information provided by measuring fluorescence from the dye. In this way, the contribution to the signal of non-specific amplification can be distinguished and thus the method provides an internal check.

Suitable reactive molecules are rhodamine dyes or other dyes such as Cy5 or fluorescein. These may be attached to the probe in a conventional manner. The position of the reactive molecule along the probe is immaterial although it general, they will be positioned at an end region of the probe.

Intercalating dyes are well known in the art. They include for example SYBRGreen such as SYBRGreen I, SYBRGold, ethidium bromide and YOPRO-1.

In order for FET, such as FRET, to occur between the reactive molecule and the dye, the fluorescent emission of the donor (which may either be the intercalating dye or the reactive molecule on the probe) must be of a shorter wavelength than the acceptor (i.e. the other of the dye or the reactive molecule).

Suitable combinations are therefore set out in the following Table:

| Dye | Acceptor/Donor | Reactive molecule | Acceptor/Donor |
| --- | --- | --- | --- |
| SYBRGold | donor | rhodamine | acceptor |
| SYBRGreen I | donor | rhodamine | acceptor |
| SYBRGold | donor | Cy5 | acceptor |
| SYBRGreen I | donor | Cy5 | acceptor |
| Ethidium bromide | acceptor | Fluorescein | donor |

Preferably, the molecules used as donor and/or acceptor produce sharp peaks, and there is little or no overlap in the wavelengths of the emission. Under these circumstances, it may not be necessary to resolve the strand specific peak from the DNA duplex binding agent signal. A simple measurement of the strand specific signal alone (i.e. that provided by the reactive molecule) will provide information regarding the extent of the FRET caused by the target reaction. The ethidium bromide/fluorescein combination may fulfil this requirement. In that case, the strand specific reaction will be quantifiable by the reduction in fluorescence at 520 nm, suitably expressed as 1/Fluorescence.

However, where there is a spectral overlap in the fluorescent signals from the donor and acceptor molecules, this can be accounted for in the results, for example by determining empirically the relationship between the spectra and using this relationship to normalize the signals from the two signals.

It is possible to design the probe such that it is hydrolyzed by the DNA polymerase used in the amplification reaction thereby releasing the reactive molecule. This provides a cumulative signal, with the amount of free reactive molecule present in the system increasing with each cycle. A cumulative signal of this type may be particularly preferred where the amount of target sequence is to be quantified. However, it is not necessary in this assay for the probe to be consumed in this way as the signal does not depend solely upon the dissociation of the probe.

In order to achieve a fully reversible signal which is directly related to the amount of amplification product present at each stage of the reaction, and/or where speed of reaction is of the greatest importance, for example in rapid PCR, it is preferable that the probe is designed such that it is released intact from the target sequence. This may be, for example, during the extension phase of the amplification reaction. However, since the signal is not dependent upon probe hydrolysis, the probe may be designed to hybridize and melt from the target sequence at any stage during the amplification cycle, including the annealing or melt phase of the reaction. Such probes will ensure that interference with the amplification reaction is minimized.

Where probes which bind during the extension phase are used, their release intact from the target sequence can be achieved by using a 5'-3' exonuclease lacking enzyme such as Stoffle fragment of Taq or Pwo.

In order to ensure that the probe is not extended during the extension phase of this, or indeed, any of the amplification reactions, the 3' end of the probe can be blocked, suitably by phosphorylation.

The probe may then take part again in the reaction, and so represents an economical application of probe.

The data generated in this way can be interpreted in various ways. In its simplest form, an increase in fluorescence of the acceptor molecule in the course of or at the end of the amplification reaction is indicative of an increase in the amount of the target sequence present, suggestive of the fact that the amplification reaction has proceeded and therefore the target sequence was in fact present in the sample. However, as outlined above, quantitation is also possible by monitoring the amplification reaction throughout. In addition, the emissions from the DNA duplex binding agent, in particular the intercalating dye, can be used in order to monitor the bulk rise in nucleic acid in the sample and this can be compared to the strand specific amplification, as measured by the relationship between the reactive molecule and dye signals. Finally, it is possible to obtain characterization data and in particular melting point analysis, either as an end point measure or throughout, in order to obtain information about the sequence as will be discussed further below.

Thus, a preferred embodiment of the invention comprises a method for detecting nucleic acid amplification comprising: performing nucleic acid amplification on a target polynucleotide in the presence of (a) a nucleic acid polymerase (b) at least one primer capable of hybridizing to said target polynucleotide, (c) a fluorescent DNA duplex binding agent and (d) an oligonucleotide probe which is capable of binding to said target polynucleotide sequence and which contains an acceptor molecule which is capable of absorbing fluorescence from the said dye; and monitoring changes in fluorescence during the amplification reaction.

As before, the DNA duplex binding agent is suitably an intercalating dye. The amplification is suitably carried out using a pair of primers which are designed such that only the target nucleotide sequence within a DNA strand is amplified as is well understood in the art. The nucleic acid polymerase is suitably a thermostable polymerase such as Taq polymerase.

Suitable conditions under which the amplification reaction can be carried out are well known in the art. The optimum conditions may be variable in each case depending upon the particular amplicon involved, the nature of the primers used and the enzymes employed. The optimum conditions may be determined in each case by the skilled person. Typical denaturation temperatures are of the order of 95° C., typical annealing temperatures are of the order of 55° C. and extension temperatures are of the order of 72° C.

The method can be used in hybridization assays for determining characteristics of particular sequences.

Thus in a further aspect, the invention provides a method for determining a characteristic of a sequence, said method comprising;

(a) adding to a sample suspected of containing said sequence, DNA duplex binding agent and a probe specific for said target sequence and, said probe comprising a reactive molecule able to absorb fluorescence from or donate fluorescent energy to said DNA duplex binding agent, (b) subjecting said sample to conditions under which the said probe hybridizes to the target sequence, (c) monitoring fluorescence from said sample and determining a particular reaction condition, characteristic of said sequence, at which fluorescence changes as a result of the hybridization of the probe to the sample or destabilization of the duplex formed between the probe and the target nucleic acid sequence.

Suitable reaction conditions include temperature, electrochemical, or the response to the presence of particular enzymes or chemicals. By monitoring changes in fluorescence as these properties are varied, information characteristic of the precise nature of the sequence can be achieved. For example, in the case of temperature, the temperature at which the probe separates or "melts" from the target sequence can be determined. This can be extremely useful in for example, to detect and if desired also to quantitate, polymorphisms in sequences including allelic variation in genetic diagnosis. By "polymorphism" is included transitions, transversions, insertions, deletions of inversions which may occur in sequences, particularly in nature.

The hysteresis of melting of the probe will be different if the target sequence varies by only one base pair. Thus where a sample contains only a single allelic variant, the temperature of melting of the probe will be a particular value which will be different from that found in a sample which contains only another allelic variant. A sample containing both allelic variants which show two melting points corresponding to each of the allelic variants.

Similar considerations apply with respect to electrochemical properties, or in the presence of certain enzymes or chemicals. The probe may be immobilized on a solid surface across which an electrochemical potential may be applied. Target sequence will bind to or be repulsed from the probe at particular electrochemical values depending upon the precise nature of the sequence.

This embodiment can be effected in conjunction with amplification reactions such as the PCR reaction mentioned above, or it may be employed individually. Again, the reactive molecule is preferably an acceptor molecule.

Further aspects of the invention include kits for use in the method of the invention. These kits will contain a probe specific for a target nucleotide sequence which contains a reactive molecule. Additionally, they may contain a DNA duplex binding agent such as an intercalating dye which is compatible in terms of being able to undergo FET or FRET with said reactive molecule. Other potential components of the kit include reagents used in amplification reactions such as DNA polymerase.

The invention will now be particularly described by way of example with reference to the accompanying diagrammatic drawings in which.

Figure 1A:
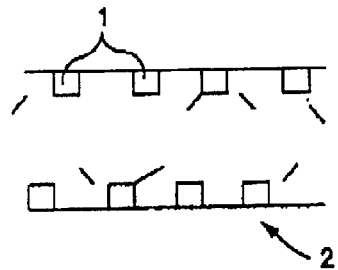
FIG. 1 shows diagrammatically the interactions which are utilised in the process of the invention.
Figure 1B:
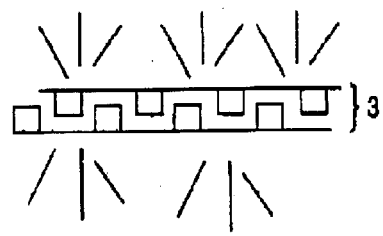

FIG. 1A illustrates the action of an intercalating dye (1) which is in the presence of single stranded DNA (2), as would be found during the melt phase of a PCR reaction. The dye attaches to the DNA strands and fluoresce at a certain level. However, when the DNA becomes double stranded (3), the dye is concentrated and the fluorescence increases significantly. This increase in fluorescence can be used to detect the formation of double stranded DNA. The fluorescence of the dye will be at a particular wavelength, for example in the green region of the spectrum.

Figure 1C:
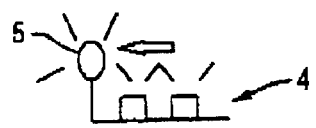

The effect of intercalating dye (1) on a probe (4) in accordance with the invention is illustrated in FIG. 1C. Some dye will bind to the nucleotides of the probe and will fluoresce at the background level. However, as a result of FRET, some energy will pass to the acceptor molecule (5) as indicated by the arrow and so this molecule will also fluoresce but at a different wavelength to that of the dye, for example, in the red region of the spectrum.

Figure 1D:
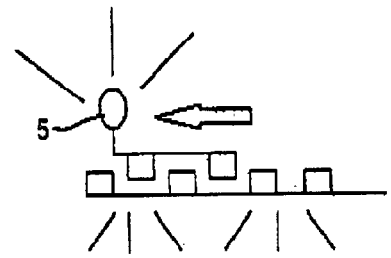

When the probe hybridizes with a single stranded target sequence as illustrated in FIG. 1D, any increase in the fluorescent energy from the dye passes to the acceptor molecule (5) which thus fluoresces at a higher level. Increase in the fluorescence of the acceptor molecule will thus be indicative of hybridization of the probe to the target sequence. Thus by measuring the increase in fluorescence of the acceptor molecule, for example as the temperature decreases, the point at which hybridization occurs can be detected. Similarly, a decrease in acceptor fluorescence will occur as the temperature increases at the temperature at which the probe melts from the target sequence. This will vary depending upon the hybridization characteristics of the probe and the target sequence. For example, a probe which is completely complementary to a target sequence will melt at a different temperature to a probe which hybridizes with the target sequence but contains one or more mismatches.

Figure 2A:
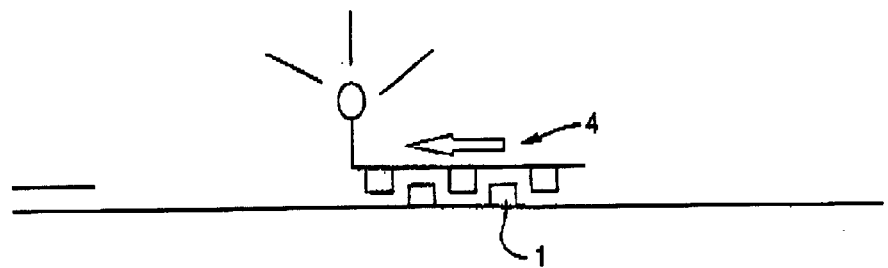
FIG. 2 illustrates stages during an amplification reaction in accordance with the invention.
Figure 2B:
Figure 2B:
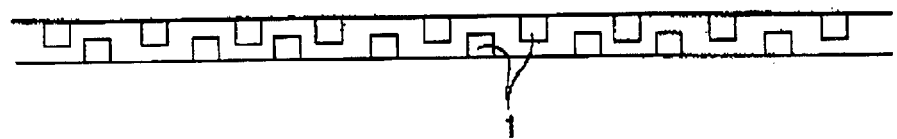
Figure 3:
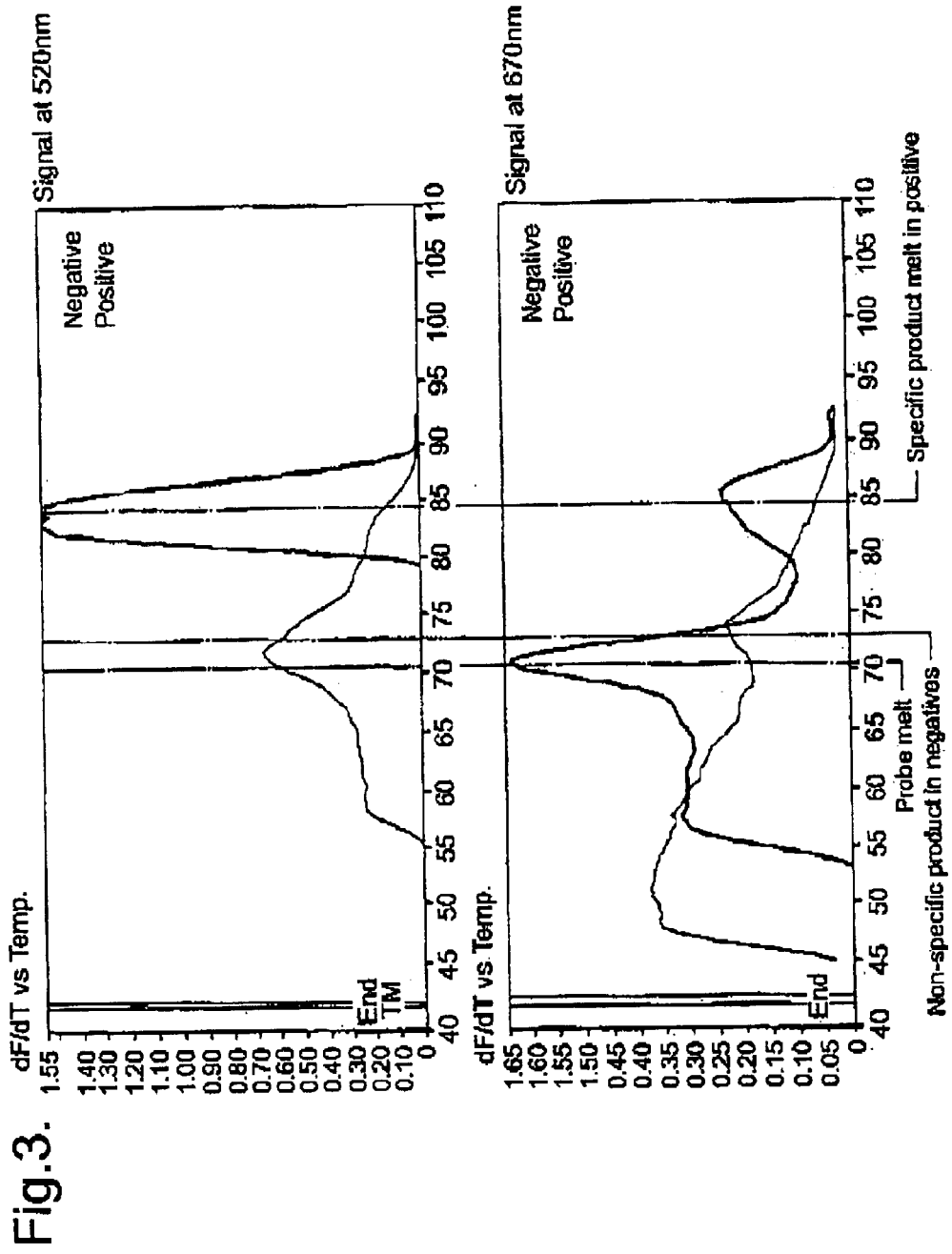
FIG. 3 shows the results of an amplification reaction in accordance with the invention.

FIG. 2 illustrates how the method of the invention can be employed in amplification reactions such as the PCR reaction. Probe (4) will hybridize to single stranded DNA in conjunction with the intercalating dye (1) and thus generate an increased acceptor signal (FIG. 2A). This will occur during the annealing phase of the cycle. As the amount of target sequence increases as a result of the amplification, the signal generated during the annealing phase by the acceptor molecule will also increase.

During the extension phase, the probe is removed from the target sequence either by hydrolysis or, as illustrated, because it is displaced by the DNA polymerase. At this point, the acceptor signal decreases although the signal from the dye (1) will be enhanced, again indicative of the increase in the amount of target sequence.

By monitoring the progress of the amplification reaction in this manner, the quantity of target sequence present in the original sample can be quantitated.

EXAMPLE 1
PCR Amplification Reaction

PCR reaction mixtures contained the following reagents, working concentrations were prepared: 1×native PCR Buffer (3mM Mg++, Bio/Gene, Bio/Gene House, 6 The Business Centre, Harvard Way, Kimbolton, Cambridge, PE18 0NJ, UK). Taq DNA polymerase 0.025 units/µl, and dNTP's PCR nucleotides 200 µM (Boehringer Mannheim UK (Diagnostics & Biochemical) Limited, Bell Lane, Lewes, East Sussex, BN7 1LG, UK). Custom oligonucleotide primers 1 µM each (Cruachem Ltd, Todd Campus, West of Scotland Science Park, Acre Road, Glasgow G20 0UA, UK). Plasmid DNA was added to a final concentration of 10 fg/µl (~3000 copies). In a negative control experiment, a similar PCR was carried out in the absence of plasmid DNA.

The forward YPPA155 (dATACGCAGAAACAGGAAGAAAGATCACCC) and reverse YPP229R (dGGTCAGAAATGAGTATGGATCCCAGGATAT) primers select a 104 bp amplicon of the anti-coagulase gene of *Yersinia pestis*. This has previously been cloned into to pBluescript SK vector (Stratagene Europe, Hogehilweg 15, 1101 CB Amersterdam, Zuidoost, The Netherlands) to form the phagemid construct pYP100 ML.

The fluorescent probe (5'(CY5) CGCTATCCTGAAAGGTGATATATCCTGG, Bio/Gene, Bio/Gene House, 6 The Business Centre, Harvard Way, Kimbolton, Cambridge, PE18 0NJ, UK) was added to a final concentration of 0.2 $\mu$M. SyberGold DYE (Molecular Probes) was added to a final concentration of 1:400,000 of the reference concentration.

The reaction was thermal cycled in composite glass capillaries and an Idaho Technology Lightcycler(Bio/Gene, Bio Gene House, 6 The Business Centre, Harvard Way, Kimbolton, Cambridge, PE18 0NJ, UK). The cycle was 95° C. for 1 Sec, 55° C. for 1 Sec, and 74° C. for 1 Sec.

Following the thermal cycle a melting experiment was carried out from 55° C. to 95° C. at 0.1° C./Sec. The reaction was optically interrogated using the LightCycler™, the fluorescent emission at 520 & 670 nm were recorded.

The results, expressed as a function of the differential of fluorescence (F) against temperature (T) dF/dT plotted against temperature on the Y axis, is shown in FIG. 3. At 520 nm, only the fluorescence from the SybrGold is recorded. A clear peak associated with the melt temperature of the specific product, which has been amplified in the PCR reaction. The negative control shows only artifacts.

At 670 nm, both signal from the CY5 acceptor molecule and also signal from the SybrGold is recorded. The peak indicative of the specific amplification product is observed in the positive experiment but is lacking in the negative control where again only artifacts are shown. However, additionally in this case, a clear peak resulting from melting of the probe is observed in the positive experiment.

EXAMPLE 2

The following materials were used.

Oligonucleotides

| | |
|---|---|
| Probe: | 5' (CY5)CGCTATCCTGAA AGGTGATATATCCTGGGA 3' |
| Homologue: | 5' TCCCAGGATATATCACC TTTCAGGATAGCG 3' |
| Mismatch 1: | 5' TCCCAGGATATATCAGC TTTCAGGATAGCG 3' |
| Mismatch 2: | 5' TCCCAGGATATATCAGG TTTCAGGATAGCG 3' |
| Mismatch 3: | 5' TCCCAGGATATATCTTT CAGGATAGCG 3' |

(Bio/Gene Limited, Bio/Gene House, 6 The Business Centre, Harvard Way, Kimbolton, Cambridgeshire, PE18 0NJ)

Intercalator

SYBR Green I (Molecular Probes)

Hybridization Buffer

PCRM0012 (Bio/Gene Limited, Bio/Gene House, 6 The Business Centre, Harvard Way, Kimbolton, Cambridgeshire, PE18 0NJ)

Fluorimeter

Idaho Technology LC32 (Bio/Gene Limited, Bio/Gene House, 6 The Business Centre, Harvard Way, Kimbolton, Cambridgeshire, PE18 0NJ)

Methods

4 $\mu$l hybridization mixtures were assembled to consist of the following:

PCRM012: Working concentration as defined by manufacturer SYBR Green I: 1/20,000 concentration of reference solution Probe oligonucleotide: 100 $\mu$M Target oligonucleotide: 100 $\mu$M Hybridization mixtures were subjected to the following temperature regime in the LightCycler. Heating to 95° C. at 20° C./s, cooling to 50° C. at 20° C./s, holding at 50° C. for 10s, heating to 80° C. at 0.1° C./s. Fluorescence was monitored in two channels during the final heating step, F1 (520 nm–580 nm) with gain set to 16 and F2 (650 nm–690 nm) with gain set to 128.

Figure 4:
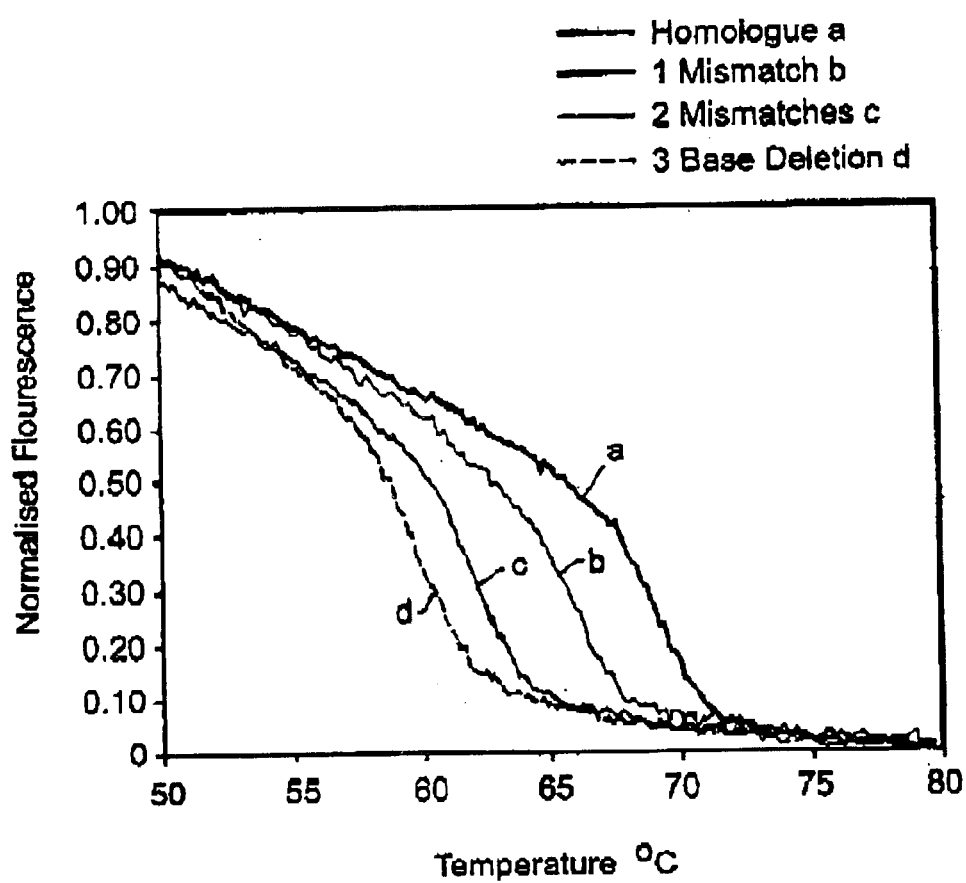
FIG. 4 shows the results of a experiment to detect mismatches in sequences.

Spectral overlap from SYBR Green I into F2 was removed from F2 fluorescence using the following empirically determined relationship: F2 overlap=0.3232×F1+ 4.2853. The SYBR Green I independent component of F2 was normalized and plotted on the Y axis against temperature on the X axis, as shown in FIG. 4. The results show the dependence of probe dissociation temperature on the nature of the sequence targeted. Single base differences in the targeted sequence are clearly discriminable.

What is claimed is:

1. A method for detecting the presence of a target nucleic acid sequence in a sample, said method comprising:
   (a) adding to a sample suspected of containing said target nucleic acid sequence, a DNA duplex binding agent, and a probe specific for said target sequence, said probe comprising a reactive molecule able to absorb fluorescence from or donate fluorescent energy to said DNA duplex binding agent, wherein the 3' end of the probe is blocked to inhibit extension thereof during the extension phase,
   (b) subjecting the thus formed mixture to an amplification reaction in which the target nucleic acid is amplified,
   (c) subjecting said sample to conditions under which the said probe hybridizes to the target sequence, and subsequently releasing said probe intact from the target sequence; and
   (d) monitoring fluorescence from said sample associated with one or both of the hybridization of the probe to the target sequence and the dissociation of the probe from the target sequence.

2. A method according to claim 1 wherein fluorescence associated with the formation and destabilization of duplexes involving the probe is determined.

3. A method according to claim 1 wherein the reactive molecule is an acceptor molecule able to absorb fluorescence from said DNA duplex binding agent.

4. A method according to claim 1 wherein the DNA duplex binding agent is an intercalating dye.

5. A method according to claim 1 wherein the target nucleic acid is rendered single stranded prior to hybridization to the probe in step (c).

6. A method according to claim 1 wherein the amplification reaction is the polymerase chain reaction (PCR).

7. A method according to claim 1 wherein the probe hybridizes with the target nucleic acid during every cycle of the amplification reaction.

8. A method according to claim 7 wherein the probe hybridizes with the target nucleic acid during a phase other than the extension phase of the amplification cycle.

9. A method according to claim 7 wherein the fluorescence from the sample is monitored throughout the amplification reaction.

10. A method according to claim 1 wherein the fluorescence from both the dye and the reactive molecule are monitored.

11. A method according to claim 1 wherein the reactive molecule is a rhodamine dye, Cy5 or fluorescein.

12. A method according to claim 1 wherein the probe is designed such that it is hydrolyzed by the DNA polymerase used in the amplification reaction.

13. A method according to claim 1 wherein the amplification reaction is effected using 5'-3' exonuclease lacking enzyme.

14. A method according to claim 1 which comprises performing nucleic acid amplification on a target polynucleotide in the presence of (a) a nucleic acid polymerase (b) at least one primer capable of hybridizing to said target polynucleotide, (c) a fluorescent DNA duplex binding agent and (d) an oligonucleotide probe which is capable of binding to said target polynucleotide sequence and which contains an acceptor molecule which is capable of absorbing fluorescence from the said DNA duplex binding agent; and monitoring changes in fluorescence during the amplification reaction.

15. A method according to claim 14 wherein the amplification is suitably carried out using a pair of amplification primers.

16. A method according to claim 14 wherein the nucleic acid polymerase is suitably a thermostable polymerase.

* * * * *

SEQUENCE LISTING

```
<160> NUMBER OF SEQ ID NOS: 8

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 1
atgacgcaga aacaggaaga aagatcagcc                                          30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 2
ggtcagaaat gagtatggat cccaggatat                                          30

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Probe

<400> SEQUENCE: 3
cgctatcctg aaaggtgata tatcctgg                                            28

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
cgctatcctg aaaggtgata tatcctggga                                          30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
tcccaggata tatcaccttt caggatagcg                                          30

<210> SEQ ID NO 6
<211> LENGTH: 30
```

```
-continued
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 6
tcccaggata tatcagcttt caggatagcg                                   30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 7
tcccaggata tatcaggttt caggatagcg                                   30

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
tcccaggata tatctttcag gatagcg                                      27
```